US012343400B2

(12) United States Patent
Lin et al.

(10) Patent No.: US 12,343,400 B2
(45) Date of Patent: Jul. 1, 2025

(54) BRAIN TUMOR-TARGETING PEPTIDE AND APPLICATION THEREOF

(71) Applicant: JIANGSU JITRI MOLECULAR ENGINEERING INST. CO., LTD., Jiangsu (CN)

(72) Inventors: Jian Lin, Jiangsu (CN); Long Chen, Jiangsu (CN); Chengpeng Li, Jiangsu (CN); Chaogang Li, Jiangsu (CN)

(73) Assignee: JIANGSU JITRI MOLECULAR ENGINEERING INST. CO., LTD., Jiangsu (CN)

( * ) Notice: Subject to any disclaimer, the term of this patent is extended or adjusted under 35 U.S.C. 154(b) by 1069 days.

(21) Appl. No.: 17/295,566

(22) PCT Filed: Jan. 17, 2020

(86) PCT No.: PCT/CN2020/072652
§ 371 (c)(1),
(2) Date: Oct. 14, 2021

(87) PCT Pub. No.: WO2020/103961
PCT Pub. Date: May 28, 2020

(65) Prior Publication Data
US 2022/0331440 A1   Oct. 20, 2022

(30) Foreign Application Priority Data

Nov. 21, 2018   (CN) .......................... 201811392953.1

(51) Int. Cl.
*A61K 47/64* (2017.01)
*A61K 31/337* (2006.01)
*A61P 35/00* (2006.01)
*C07K 14/00* (2006.01)

(52) U.S. Cl.
CPC ............ *A61K 47/64* (2017.08); *A61K 31/337* (2013.01); *A61P 35/00* (2018.01)

(58) Field of Classification Search
CPC ....... A61K 47/64; A61K 31/337; A61P 35/00; C07K 14/00
See application file for complete search history.

(56) References Cited

FOREIGN PATENT DOCUMENTS

| CN | 101143895 A | 3/2008 |
|---|---|---|
| CN | 103083689 A | 5/2013 |
| CN | 103254280 A | 8/2013 |
| CN | 106699845 A | 5/2017 |
| CN | 107029239 A | 8/2017 |
| CN | 108570108 A | 9/2018 |
| CN | 108743953 A | 11/2018 |
| CN | 109666973 A | 4/2019 |
| CN | 109678966 A | 4/2019 |

OTHER PUBLICATIONS

International Search Report dated Apr. 22, 2020 issued in PCT/CN2020/072652.
Chinese Office Action dated Mar. 25, 2020 issued in CN 201811392953.1.
Chen, C. et al., "Peptide-22 and Cyclic RGD Functionalized Liposomes for Glioma Targeting Drug Delivery Overcoming BBB and BBTB", ACS Applied Materials & Interfaces (Feb. 22, 2017), vol. 9, No. 7, pp. 5864-5873.
Gao, Huile, (Non-official translation: "Design and Evaluation of Brain Tumor Targeting Delivery System Based on Different Targeting Strategies"), Chinese Doctoral Dissertations Full-Text Database, Medical and Health Sciences (Mar. 15, 2015), No. 3.

*Primary Examiner* — Amber D Steele
(74) *Attorney, Agent, or Firm* — Scully, Scott, Murphy & Presser, P.C.

(57) ABSTRACT

The present invention related to a brain tumor-targeting peptide, a coding nucleic acid thereof, and a vector and host cell comprising the coding nucleic acid. The targeting peptide linked to a diagnostic marker can be used in brain tumor diagnosis, especially in brain tumor imaging; and the targeting peptide when linked to a therapeutic drug can carry the drug directly to a brain tumor lesion so as to achieve brain tumor treatment.

15 Claims, 7 Drawing Sheets

Specification includes a Sequence Listing.

SEQUENCE LISTING

<160> NUMBER OF SEQ ID NOS: 8

<210> SEQ ID NO 1
<211> LENGTH: 21
<212> TYPE: PRT
<213> ORGANISM: Artificial Sequence
<220> FEATURE:
<223> OTHER INFORMATION: peptide

<400> SEQUENCE: 1

Thr Phe Tyr Gly Gly Arg Pro Lys Arg Asn Asn Phe Leu Arg Gly Ile
1               5                   10                  15

Arg Ser Arg Gly Asp
            20

<210> SEQ ID NO 2
<211> LENGTH: 17
<212> TYPE: PRT
<213> ORGANISM: Artificial Sequence
<220> FEATURE:
<223> OTHER INFORMATION: peptide

<400> SEQUENCE: 2

Thr Phe Tyr Gly Gly Arg Pro Lys Arg Asn Asn Phe Leu Arg Gly Ile
1               5                   10                  15

Arg

<210> SEQ ID NO 3
<211> LENGTH: 5
<212> TYPE: PRT
<213> ORGANISM: Artificial Sequence
<220> FEATURE:
<223> OTHER INFORMATION: peptide

<400> SEQUENCE: 3

Cys Gly Lys Arg Lys
1               5

<210> SEQ ID NO 4
<211> LENGTH: 8
<212> TYPE: PRT
<213> ORGANISM: Artificial Sequence
<220> FEATURE:
<223> OTHER INFORMATION: peptide

<400> SEQUENCE: 4

Ala Thr Trp Leu Leu Pro Pro Arg
1               5

<210> SEQ ID NO 5
<211> LENGTH: 22
<212> TYPE: PRT
<213> ORGANISM: Artificial Sequence
<220> FEATURE:
<223> OTHER INFORMATION: peptide

<400> SEQUENCE: 5

Thr Phe Tyr Gly Gly Arg Pro Lys Arg Asn Asn Phe Leu Arg Gly Ile
1               5                   10                  15

Arg Cys Gly Lys Arg Lys
            20

<210> SEQ ID NO 6
<211> LENGTH: 25
<212> TYPE: PRT

```
<213> ORGANISM: Artificial Sequence
<220> FEATURE:
<223> OTHER INFORMATION: peptide

<400> SEQUENCE: 6

Thr Phe Tyr Gly Gly Arg Pro Lys Arg Asn Asn Phe Leu Arg Gly Ile
1               5                   10                  15

Arg Ala Thr Trp Leu Leu Pro Pro Arg
            20                  25

<210> SEQ ID NO 7
<211> LENGTH: 9
<212> TYPE: PRT
<213> ORGANISM: Artificial Sequence
<220> FEATURE:
<223> OTHER INFORMATION: peptide

<400> SEQUENCE: 7

Cys Arg Gly Asp Lys Gly Pro Asp Cys
1               5

<210> SEQ ID NO 8
<211> LENGTH: 26
<212> TYPE: PRT
<213> ORGANISM: Artificial Sequence
<220> FEATURE:
<223> OTHER INFORMATION: peptide

<400> SEQUENCE: 8

Thr Phe Tyr Gly Gly Arg Pro Lys Arg Asn Asn Phe Leu Arg Gly Ile
1               5                   10                  15

Arg Cys Arg Gly Asp Lys Gly Pro Asp Cys
            20                  25
```

BRAIN TUMOR-TARGETING PEPTIDE AND APPLICATION THEREOF

INCORPORATION BY REFERENCE OF SEQUENCE LISTING

The Sequence Listing in an ASCII text file, named 39634_SubstituteSequenceListing.txt of 3,000 bytes, created on Oct. 15, 2024, and submitted to the United States Patent and Trademark Office via Patent Center, is incorporated herein by reference.

TECHNICAL FIELD

The present disclosure relates to the field of biomedical engineering, in particular to a protein detection drug or a therapeutic drug, and specifically to a peptide that can efficiently cross the blood-brain barrier and target brain tumors, as well as use of the peptide in in-vivo imaging detection and targeted therapy of brain tumors.

BACKGROUND

As a high-level nerve center of human, the brain has a unique protective mechanism. i.e., the blood-brain barrier, which restricts the entry of many substances into the brain. There is a blocking mechanism of the blood-brain barrier between the brain and the outside for strictly restricting the entry of substances, which makes it difficult for most of the currently effective drugs to reach the target so that it is difficult to effectively treat brain diseases.

RGD is a short peptide sequence containing arginine-glycine-aspartic acid (Arg-Gly-Asp), which acts as a recognition site for the interaction of integrins and its ligands, and mediates the interaction between cells and extracellular matrix as well as between cells. Tumor cells or new blood vessels can specifically express certain integrins such as $\alpha v \beta 3$, which can bind to RGD peptide with a certain affinity and become a new target for tumor treatment. Therefore, the application of RGD peptide in tumor treatment has become a research hotspot. This short peptide not only has the ability to cross the blood-brain barrier, but also plays a certain role in specifically targeting brain tumors. At the same time, some other short peptides targeting highly expressed antigens on the tumor surface may also have similar functions.

At present, the therapeutic drugs for brain tumors are limited by the action of the blood-brain barrier. The only drug that can well cross the blood-brain barrier is temozolomide, but its effectiveness is limited. As a short peptide vector that can efficiently cross the blood-brain barrier. Pb001 short peptide can carry other drugs through the blood-brain barrier, which will greatly improve the scope and efficacy of the use of brain drugs.

SUMMARY

In order to solve the above problems, based on the idea of receptor-mediated pathway, the receptor pathway mediated by receptor LRP1 can be used to select a skeleton by referring to a bovine pancreatic islet inhibitor and a protein-conserved active center kunitz region of β-amyloid peptide crossing the blood-brain barrier; using a phage display technology, a high-throughput phage display library is constructed through in vitro artificial synthesis to obtain a short peptide that can efficiently cross the blood-brain barrier with new proprietary intellectual property rights from the foundation; mouse in vivo screening technology is used to optimize the screening process, and a short peptide that can efficiently cross the blood-brain barrier is obtained through three rounds of screening. On this basis, a targeting molecule that can efficiently cross the blood-brain barrier is obtained through further design, the C-terminus of which contains tumor target region sequences.

In a first aspect, the present disclosure provides a brain tumor targeted molecule, which is characterized by including a blood-brain barrier crossing region and a tumor target region, and the blood-brain barrier crossing region includes TFYGGRPKRNNFLRGIRSRGD (SEQ ID NO: 1).

According to different factors such as hydrophilicity, the tumor target region can have different molecular sizes. A basic principle is that the higher the hydrophilicity is, the smaller the size of the molecule suitable for serving as a brain tumor target region will be; and the lower the hydrophilicity is, the larger the size of the molecule suitable for serving as the brain tumor target region will be. As an example, for hydrophilic molecules (such as linear peptides, cyclic peptides and other peptide derivatives), the tumor target region serving as the brain tumor targeted peptide may include no more than 100, 50, 40, 30, 20, 15, or 10 amino acids.

Through routine experiments, those skilled in the art can detect and verify the ability and efficiency of the tumor target region and the SEQ ID NO:1 blood-brain barrier crossing peptide to cross the blood-brain barrier after being connected by peptide bonds. After the SEQ ID NO: 1 blood-brain barrier crossing region of the present disclosure is connected to the tumor target region, the ability of SEQ ID NO:1 to cross the blood-brain barrier is at least partially retained.

The at least partially retaining the ability of SEQ ID NO:1 to cross the blood-brain barrier includes for example retaining at least 10%, 20%, 30%, 40%, 50%, 60%, 70%, 80%, 90%, 95%, or 98% of the ability of SEQ ID NO: 1 to cross the blood-brain barrier.

The brain tumor targeted molecule can be obtained by connecting the blood-brain barrier crossing region to any polypeptide with a tumor targeting function.

In a specific embodiment, the tumor target region includes any one of or a combination of CGKRK (SEQ ID NO: 3) and ATWLLPPR (SEQ ID NO: 4).

Further, the amino acid sequence of the brain tumor targeted molecule is TFYGGRPKRNNFLRGIRCGKRK (SEQ ID NO: 5) or TFYGGRPKRNNFLRGIRATWLLPPR (SEQ ID NO: 6).

The brain tumor targeted molecule of the present disclosure is characterized in that: the tumor target region includes an RGD sequence.

Further, the RGD sequence is a linear RGD polypeptide, a cyclic GRD polypeptide or a peptidomimetic compound with an arginine-glycine-aspartic acid tripeptide sequence as an active center. In a specific embodiment, the sequence of the cyclic RGD polypeptide is CRGDKGPDC (SEQ ID NO: 7), in which two cysteines form a disulfide bond.

The brain tumor targeted molecule of the present disclosure is characterized in that the amino acid sequence of the brain tumor targeted peptide is shown in SEQ ID NO: 2 (TFYGGRPKRNNFLRGIR).

In another embodiment, the amino acid sequence of the brain tumor targeted peptide is TFYGGRPKRNNFLRGIR-CRGDKGPDC (SEQ ID NO: 8)

In a second aspect, the present disclosure also provides a nucleic acid encoding the brain tumor targeted molecule.

In a third aspect, the present disclosure provides a construct including the encoding nucleic acid, and the construct includes nucleic acid expression cassettes and vectors.

The vector of the present disclosure includes prokaryotic expression vectors and eukaryotic expression vectors.

In a fourth aspect, the present disclosure also provides a host cell containing the encoding nucleic acid and the nucleic acid construct.

The host cell of the present disclosure includes prokaryotic host cells and eukaryotic host cells; the prokaryotic host cells include *Escherichia coli*, and the eukaryotic host cells include *Pichia pastoris, Saccharomyces cerevisiae*, insect cells and the like.

In a fifth aspect, the present disclosure also provides the use of the brain tumor targeted molecule in the preparation of a brain tumor diagnostic reagent.

The brain tumor targeted molecule is also connected with an active substance, and the active substance is a diagnostic marker.

The diagnostic marker includes fluorescence, isotopes, radioactive substances, etc.

The brain tumor diagnostic reagent is used for brain tumor imaging or brain tumor localization.

In a sixth aspect, the present disclosure also provides the use of the brain tumor targeted molecule in the preparation of a brain tumor therapeutic drug.

The brain tumor targeted molecule is also connected with an active substance, and the active substance is a therapeutic drug.

The therapeutic drug includes chemotherapeutic drugs, radioactive substances, etc.

The brain tumor targeted molecule is used for targeted therapy of brain tumor.

According to different factors such as hydrophilicity, the active substance connected to the brain tumor targeted molecule can have different molecular sizes. A basic principle is that the higher the hydrophilicity is, the smaller the molecular size of the active substance suitable for connecting to the brain tumor targeted molecule will be; and the lower the hydrophilicity is, the larger the molecular size of the active substance suitable for connecting to the brain tumor targeted molecule will be.

Through routine experiments, those skilled in the art can detect and verify the ability and efficiency of the active substances (such as tumor diagnostic or therapeutic drugs) to cross the blood-brain barrier after being connected to the brain tumor targeted molecule. Preferably, after being connected to the active substances such as diagnostic or therapeutic drugs, the brain tumor targeted molecule of the present disclosure at least partially retains the ability of the brain tumor targeted molecule to cross the blood-brain barrier before being connected to the active substances.

The at least partially retaining the ability of the brain tumor targeted peptide to cross the blood-brain barrier before being connected to the active substances includes for example retaining at least 10%, 20%, 30%, 40%, 50%, 60%, 70%, 80%, 90%, 95%, or 98% of the ability of the brain tumor targeted molecule of the present disclosure to cross the blood-brain barrier before being connected to the active substances.

As compared with the prior art, the technical solutions of the present disclosure have the following advantages:

First, the blood-brain barrier crossing part contained in the Pb001 peptide provided by the present disclosure is obtained through animal model in vivo screening. As compared with in vitro screening methods, the animal model in vivo screening is closer to the real process of crossing the blood-brain barrier in human body. It is ensured that the Pb001 peptide of the present disclosure has a function of efficiently crossing the blood-brain barrier in vivo.

Second, by combining the efficient blood-brain barrier crossing peptide obtained by screening with RGD, the present disclosure achieves the functions of crossing the blood-brain barrier and targeting tumor at the same time, thereby providing a new vector and platform for the diagnosis and treatment of brain tumors.

Third, the Pb001 peptide of the present disclosure is composed of only 21 amino acids, and has a small molecule and a great prospect of modification, so it can carry various diagnostic imaging agents, radiotherapy agents, and chemotherapeutic agents to target brain tumors.

BRIEF DESCRIPTION OF THE DRAWINGS

Upon reading a detailed description of preferred embodiments below, various other advantages and benefits will become clear to those skilled in the art. The drawings are only used for the purpose of illustrating the preferred embodiments, and should not be considered as limiting the present disclosure. In the drawings.

DETAILED DESCRIPTION

Figure 1:
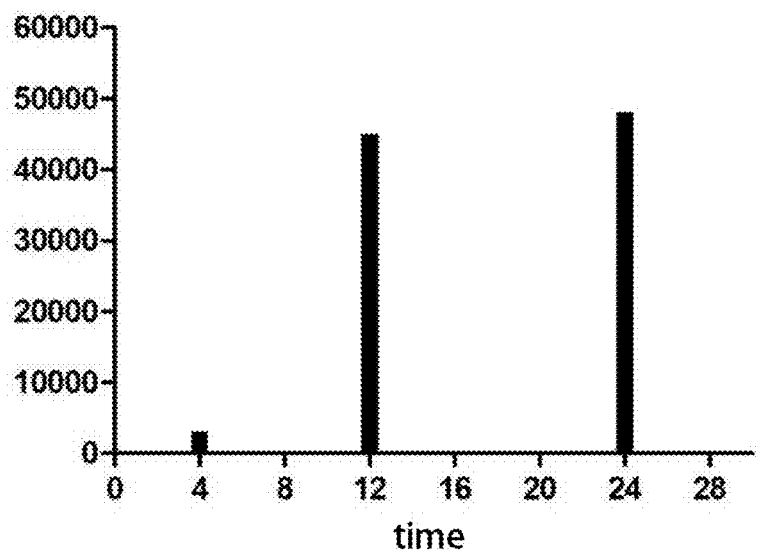
FIG. 1 shows the best enrichment time after administration of phage display peptides into mouse brains.

Hereinafter, exemplary embodiments of the present disclosure will be described in more detail with reference to the accompanying drawings. Although the exemplary embodiments of the present disclosure are shown in the drawings, it should be understood that the present disclosure may be implemented in various forms and should not be limited by the embodiments set forth herein. On the contrary, these embodiments are provided to enable a more thorough understanding of the present disclosure and to fully convey the scope of the present disclosure to those skilled in the art.

According to the embodiments of the present disclosure, the following examples are proposed.

Example 1: Screening Out Efficient Blood-Brain Barrier Crossing Peptides by Using Animal In Vivo Screening Method Based on the sequence analysis of an active center kunitz region, a peptide library kun-M, which is a phage-displayed peptide library, was designed and constructed. This library is used for high-throughput screening.

The screening method is performed as follows.

1. For adult balb/c mice (18-22 g), the phage library TBS is taken and diluted to 100 ul/1011 PFU, and then injected into tail veins of the mice. According to preliminary experiments, it is determined that the enrichment cerebrovaso ratio of the phage in the brain is the highest 24 h after inoculation (see FIG. 1).

2. The mice were anesthetized with 5% chloral hydrate 24 h after the injection, the surface of the mice was wiped with alcohol, and disinfected, 100 ml of normal saline was flowed through the heart, the brain was carefully dissected, the brain reticulum homogenate was ultrasonically broken, centrifuged, and passed through a 0.45 μm filter membrane, the supernatant solution was taken and blended with the ER2738 bacterial solution cultured to the logarithmic phase, and was infected and cultured at 37° C. for 4 h.

3. After centrifugation at 12000 rpm for 20 minutes, the supernatant of the bacterial solution was taken, the phage was enriched using the PEG/NaCl method, and the enriched library was used for the next round of screening.

4. The above process was repeated for at least three rounds. After seeing that the titers of the output phage were obviously enriched, the phage may be taken to infect the clones, which were then sent for sequence analysis to display the sequence of the polypeptide nanobody.

The highest-frequency sequence screened out was: TFYGGRPKRNNFLRGIR (SEQ ID NO:2).

The C-terminus of TFYGGRPKRNNFLRGIR (SEQ ID NO:2) was connected to the tumor target region sequence to obtain a brain tumor targeted peptide that can cross the blood-brain barrier.

On this basis, the brain tumor targeted peptide Pb001 that can cross the blood-brain barrier was designed and synthesized:

TFYGGRPKRNNFLRGIRSRGD (SEQ ID NO:1).

In addition, polypeptides TFYGGRPKRNNFLRGIR-CRGDKGPDC (SEQ ID NO:8) (two cysteines form a disulfide bond), TFYGGRPKRNNFLRGIRCGKRK (SEQ ID NO:5) and TFYGGRPKRNNFLRGIRATWLLPPR (SEO ID NO:6) were designed and synthesized.

Example 2: Synthesis and Function Verification of Brain Tumor Targeted Peptides

1. Chemical Synthesis of Polypeptides and Fluorescent Labels

Figure 2:
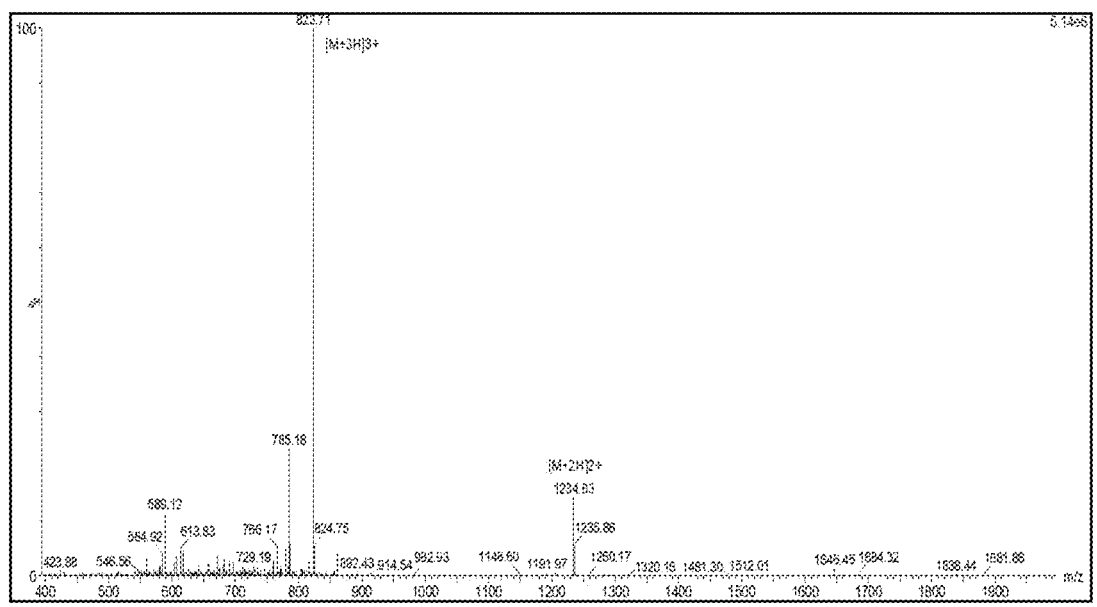
FIG. 2 shows a mass spectrometry detection diagram of synthesized Pb001 peptide.

The polypeptide TFYGGRPKRNNFLRGIRSRGD (SEO) ID NO: 1) (MW: 2467.78 PI: 11.83) was synthesized, the mass spectrometry detection results of the unlabeled polypeptide were shown in FIG. 2. According to FIG. 2, the calculated molecular weight was 823.71*3−3=2468, which was consistent with the molecular weight of the polypeptide Pb001.

The Pb001 was labeled with CY5.5 fluorescence, the short peptide was fluorescently labeled with the Cyanine5.5 NHS ester labeling reagent of the Lumiprobe brand, and one short peptide was labeled with one fluorescent molecule.

2. Enrichment of Fluorescently Labeled Pb001 in the Brains of Normal Mice.

The concentration of the labeled short peptide was accurately diluted and adjusted, and was dissolved with normal saline, the fluorescently labeled short peptide was adjusted and diluted to the same amount of fluorescence equivalent, and 100 μl was injected into the tail veins of nude mice. At different time points, the small animal in vivo imaging system IVIS was used for observing the imaging at different time points.

Figure 3:
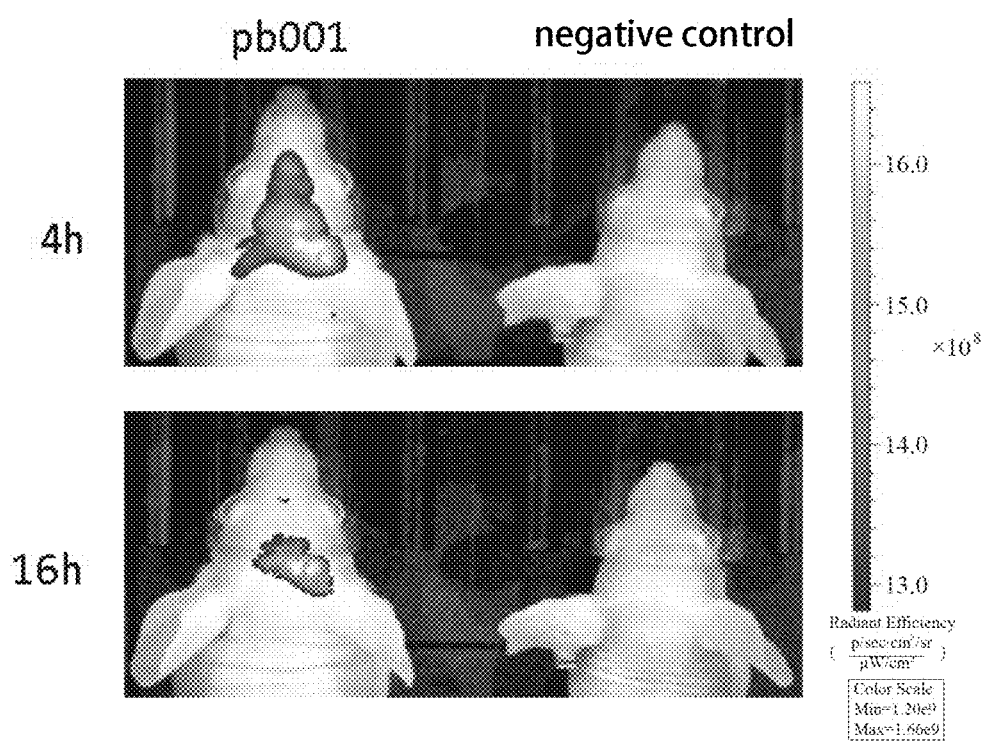
FIG. 3 shows a brain enrichment image of fluorescently labeled Pb001 peptide.
Figure 4:
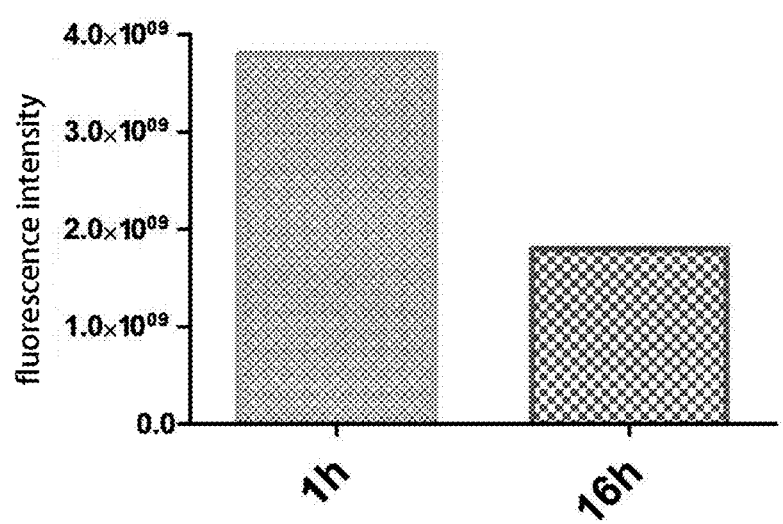
FIG. 4 shows a residual fluorescence intensity of the fluorescently labeled Pb001 peptide in the brain.

As shown in FIG. 3, it can be obviously observed that Pb001-CY5.5 was enriched in the brain 4 h after tail vein injection. The mice were taken. 100 ml of normal saline was flowed through the heart at a speed of 5 ml/min to wash off the fluorescence interference in the blood. The brains and other organs of the mice were taken and observed. It can be seen that the brain has obvious fluorescence, which is higher than those of the muscle, the heart and the like. After 16 hours overnight, the presence of fluorescence in the mouse brain can still be clearly seen, and the fluorescence value is only reduced by 40% (FIG. 4). It shows that the short peptide can pass through the blocking of the blood-brain barrier and have an ability to efficiently cross the blood-brain barrier. The fluorescence of the short peptide has a strong retention time in the brain and has a better half-life.

3. Establishing a Tumor Model and Checking the Enrichment of Fluorescent Short Peptides in the Tumor.

u87 brain glioma cells were cultivated. When the cells grew to a sufficient amount, the cells were taken, 8-weeks old nude mice were selected, the brains were located, and 5× $10^5$ cells were injected at the location for brain tumorigenesis. U87 tumorigenesis cell line is a cell line with luciferase gene transferred, and the mouse imager can be used to observe the tumorigenesis effect in real time.

After tumorigenesis of the tumor model mice became stable, 100 μl of solution of short peptides labeled with fluorescent molecules was injected into the tail veins. A short peptide Angiopep 2, which was from the Angiochem company and was reported in an article to be able to cross the blood-brain barrier, was selected as a reference control. It is currently reported that this short peptide has excellent applications in crossing the blood-brain barrier and targeting brain tumors. The negative control was fluorescent molecule cy5.5 of the same amount of fluorescence equivalent. After the tail vein injection, the small animal in vivo imaging system IVIS was used to check the brain fluorescence. 100 μl of 5 mg/ml luciferase reaction substrate was injected into the intraperitoneal cavity. After 5 minutes, the small animal imaging system was used to check the brain tumors.

Figure 5:
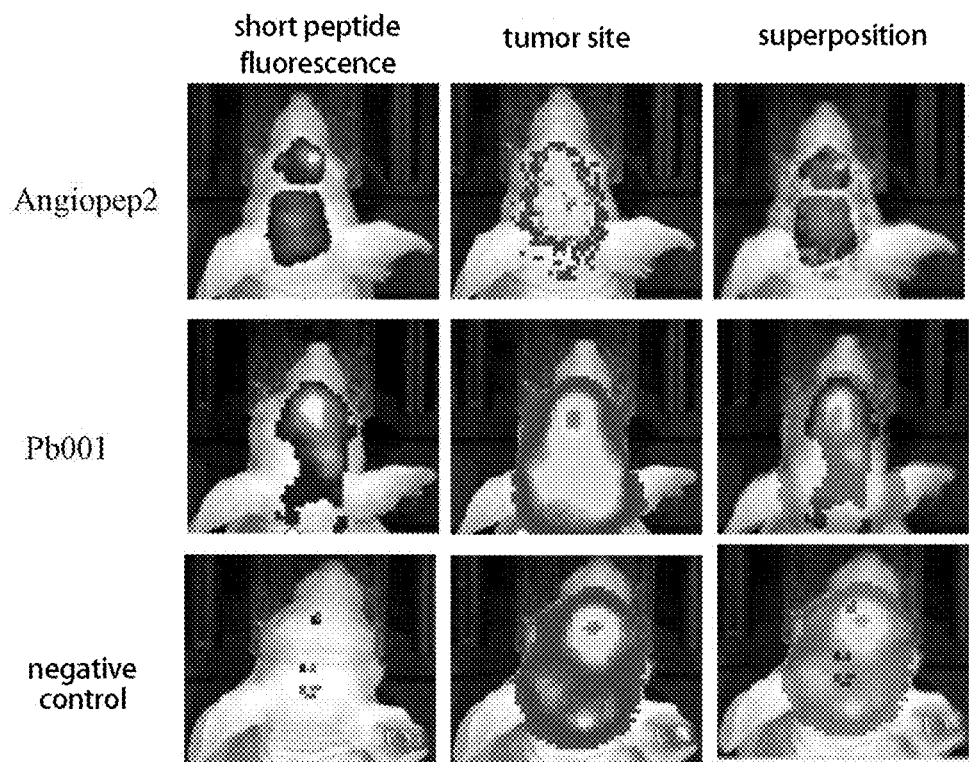
FIG. 5 shows the fluorescently labeled Pb001 peptide crossing the blood-brain barrier and tumor localization.
Figure 6:
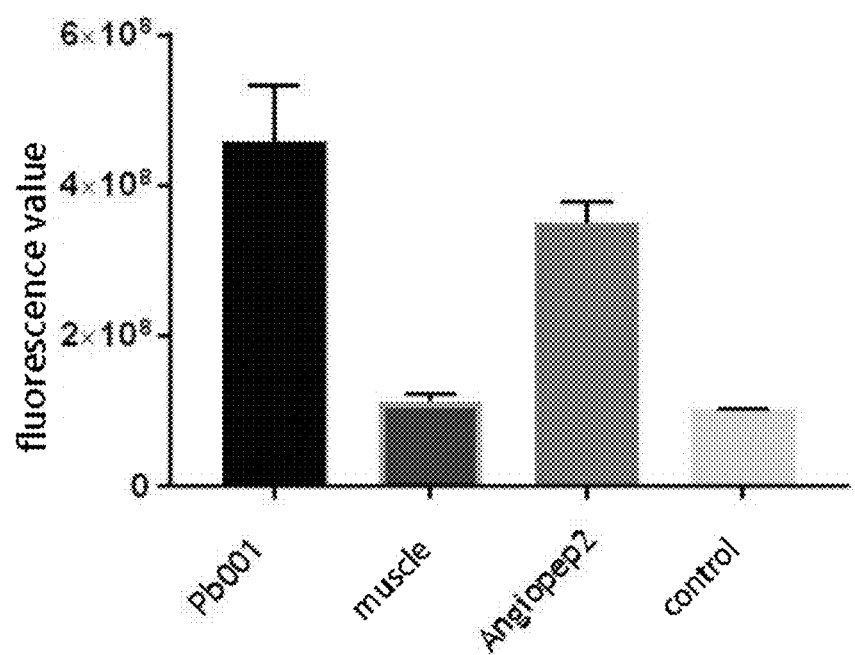
FIG. 6 shows a fluorescence intensity of the fluorescently labeled Pb001 peptide in the brain.

After the pb001 short peptide was connected to the fluorescence, it can be enriched in the brain of brain glioma model mice, and 100 ml of normal saline was flowed through the heart at a speed of 5 ml/min to wash off the fluorescence interference in the blood. The brains of the mice were taken and the fluorescence of the brains was compared. FIG. 5 shows that the brain enrichment amount of the fluorescently labeled Pb001 peptide is better than that of the fluorescently labeled reference peptide Angiopep2. FIG. 6 shows that the fluorescence intensity of the fluorescently labeled Pb001 peptide is 1.2 times that of the fluorescently labeled reference peptide Angiopep2.

Figure 7:
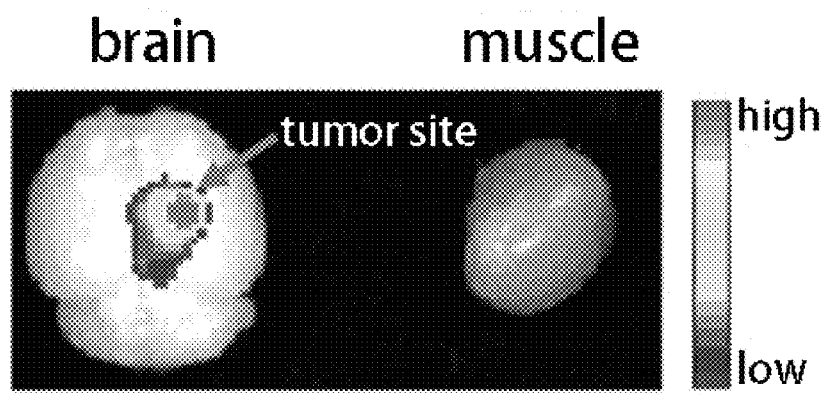
FIG. 7 shows localization and enrichment of the fluorescently labeled Pb001 peptide in brain tumors.

FIG. 7 shows that the fluorescently labeled Pb001 peptide has obvious fluorescence accumulation in the brain tumor site, that is, Pb001 can not only cross the blood-brain barrier, but also has a better enrichment for brain tumors.

Example 3: Enrichment Factor of Brain Tumor Targeted Peptide in the Brain

Polypeptides TFYGGRPKRNNFLRGIR (SEQ ID NO:2), TFYGGRPKRNNFLRGIRCRGDKGPDC (SEQ ID NO:8) (two cysteines form a disulfide bond), TFYGGRPKRNNFLRGIRCGKRK (SEQ ID NO:5) and TFYGGRPKRNNFLRGIRATWLLPPR (SEQ ID NO:6) were respectively synthesized by solid-phase polypeptide synthesis. Cyanine5.5 NHS ester labeling reagent of the Lumiprobe brand was used to fluorescently label each short peptide, and each short peptide was labeled with one fluorescent molecule. After the labeling was completed, these short peptides and the Pb001 also labeled with CY5.5 in Example 2 were respectively injected into the tail veins of different mice with the U87 brain tumors; after 2 hours, the mice were dissected and the brains were taken. The fluorescence intensity per unit area was calculated for the brain tumor site and other brain sites respectively, and the enrichment factor of the corresponding polypeptide at the tumor site can be obtained by dividing the fluorescence intensity per unit area at the brain tumor site by the fluorescence intensity per unit area at other brain sites.

Figure 8:
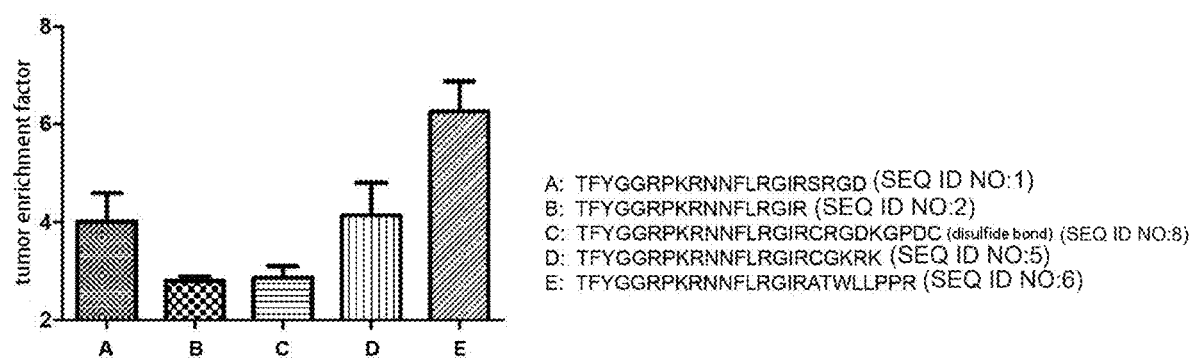
FIG. 8 shows an enrichment factor of each fluorescently labeled and brain tumor targeted peptide at the brain tumor site.

As shown in FIG. 8, as compared to the TFYGGRPKRNNFLRGIR (SEQ ID NO:2) peptide having no tumor targeted peptide connected, the other peptides all showed better tumor enrichment. The tumor targeted sequence (CGKRK (SEQ ID NO:3), ATWLLPPR (SEQ ID NO: 4)) contained in the TFYGGRPKRNNFLRGIRCGKRK (SEQ ID NO:5) and TFYGGRPKRNNFLRGIRATWLLPPR (SEQ ID NO:6) peptides binds to different targets from the RGD sequence. Therefore, it can be seen that tumor targeted peptides targeting different receptors on the brain tumor surface can each be connected to the C-terminus of the peptide TFYGGRPKRNNFLRGIR (SEQ ID NO:2) that crosses the blood-brain barrier, thus enabling them to have the ability to cross the blood-brain barrier and the ability to target tumors at the same time.

As compared with the TFYGGRPKRNNFLRGIR (SEQ ID NO:2) peptide, the increase in brain tumor enrichment of TFYGGRPKRNNFLRGIRCRGDKGPDC (SEQ ID NO: 8) is not as significant as the other three synthesized polypeptides. The possible reason is that the cyclic peptide structure of the tumor targeted sequence CRGDKGPDC (SEQ ID NO:7) has a certain influence on the structure of the TFYGGRPKRNNFLRGIR (SEQ ID NO:2) peptide. The influence can be eliminated by adjusting the connecting sequence between the two peptide sequences. In addition, the experimental results of TFYGGRPKRNNFLRGIRCRGDKGPDC (SEQ ID NO:8) in FIG. 8 also show that the blood-brain barrier crossing peptide TFYGGRPKRNNFLRGIR (SEO ID NO: 2) can not only carry shorter peptides (such as short peptides having a length less than or equal to 5 amino acids), but also are suitable for carrying larger molecules, longer peptides, cyclic peptide structures and the like to cross the blood-brain barrier; even if connected with a cyclic peptide containing 10 amino acids, it will not significantly affect the efficiency of crossing the blood-brain barrier.

Example 4. Synthesis and In Vitro and In Vivo Characterization of Polypeptide-Paclitaxel Conjugated Drug PBL001

1. Synthesis of PBL001

Figure 9:
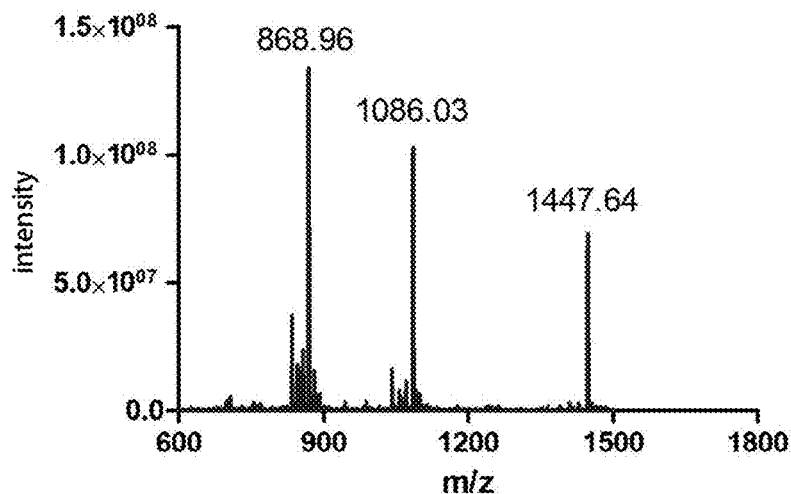
FIG. 9 shows mass spectrum results of PBL001 which is a polypeptide-paclitaxel conjugate of Pb001 and drug paclitaxel.
Figure 10:
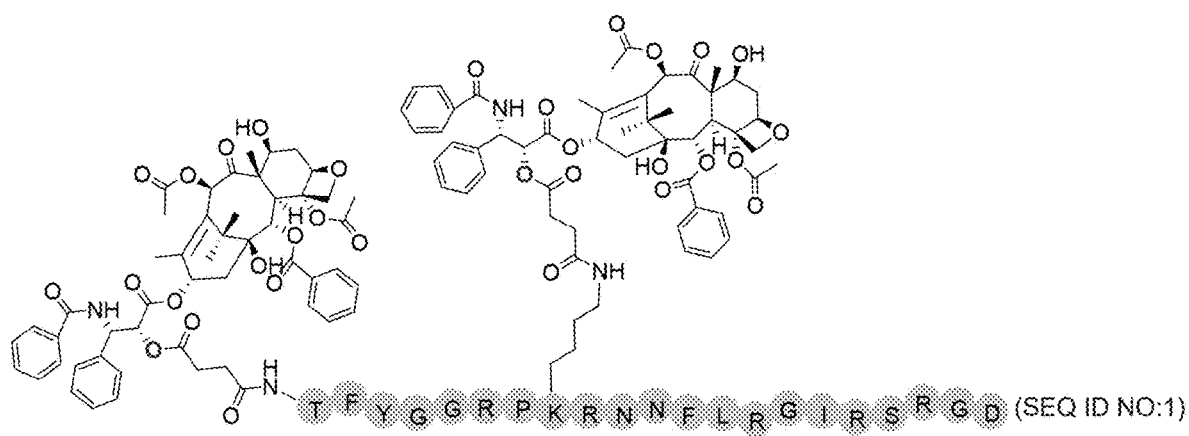
FIG. 10 shows a schematic diagram of the structure of PBL001.

The synthesized polypeptide Pb001 was dissolved in DMF (N, N-dimethylformamide), and the paclitaxel molecules were synthesized into 2'-NHS-Paclitaxel according to the literature (British Journal of Pharmacology, 2008, 155 (2): 185-197.). Pb001, 2'-NHS-Paclitaxel, and triethylamine (or N, N-diisopropylethylamine) were mixed in a ratio of 1:5:5, reacted at 37° C. for 3 hours, and purified by HPLC to obtain PBL001. The mass spectrometry results were shown in FIG. 9, and the schematic structural diagram was shown in FIG. 10. Each PBL001 molecule contained 2 paclitaxel molecules, with a theoretical molecular weight of 4339.75.

2. In Vitro Inhibition of the Proliferation of U87MG Brain Glioma by PBL001

Figure 11:
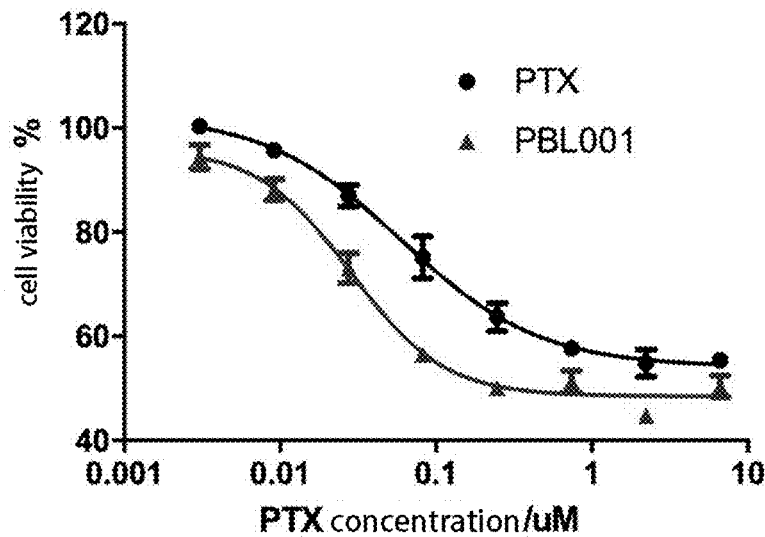
FIG. 11 shows that PBL001 inhibits proliferation of U87MG brain glioma cells at different concentrations in vitro.

On the first day, 2000 U87MG cells were inoculated in a 96-well plate, and the cells were treated with paclitaxel (PTX) or PBL001 at different concentrations on the second day. Cell viability was determined two days later, and the tumor proliferation inhibition curve as shown in FIG. 11 was obtained. The results in FIG. 11 showed that the PBL001 obtained by coupling the pb001 short peptide with paclitaxel did not reduce the anti-brain glioma activity of paclitaxel, and the activity was even increased slightly. It is speculated that the possible reason was that the modified PBL001 can penetrate the cell membrane more easily.

Figure 12:
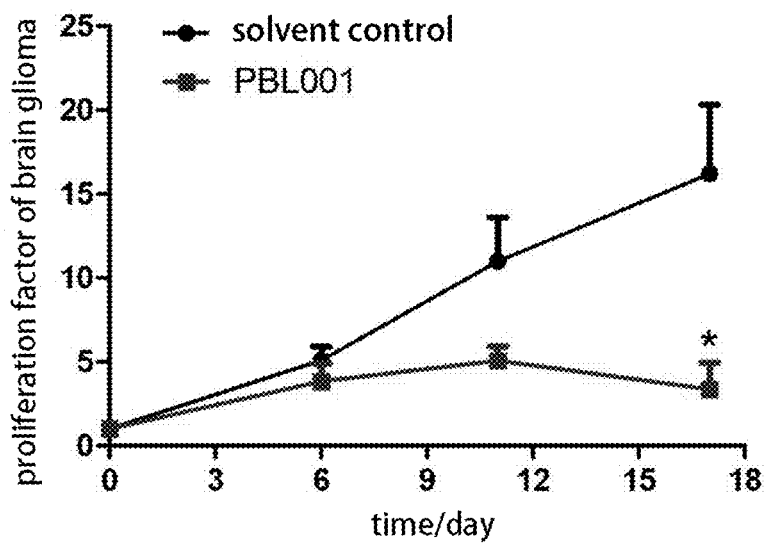
FIG. 12 shows that PBL001 inhibits proliferation of U87MG brain glioma tumors in a mouse model in vivo.

3. In Vivo Inhibition of the Tumor Proliferation of U87MG Brain Glioma by PBL001 in a Mouse Model On the first day, $10^6$ U87MG cells were inoculated at the right caudate nucleus of nude mice of 6-8 weeks old. Three days later, PBL001 was administered via the tail vein. U87MG cells were stably transfected with the luciferase gene, and chemiluminescence by luciferase was used to determine the proliferation of brain tumors, as shown in FIG. 12. The results in FIG. 12 showed that PBL001 had a significant inhibitory effect on the proliferation of brain glioma in the mouse model.

4. Prolonging the Survival Time of the Brain Glioma Model Mice by PBL001

Figure 13:
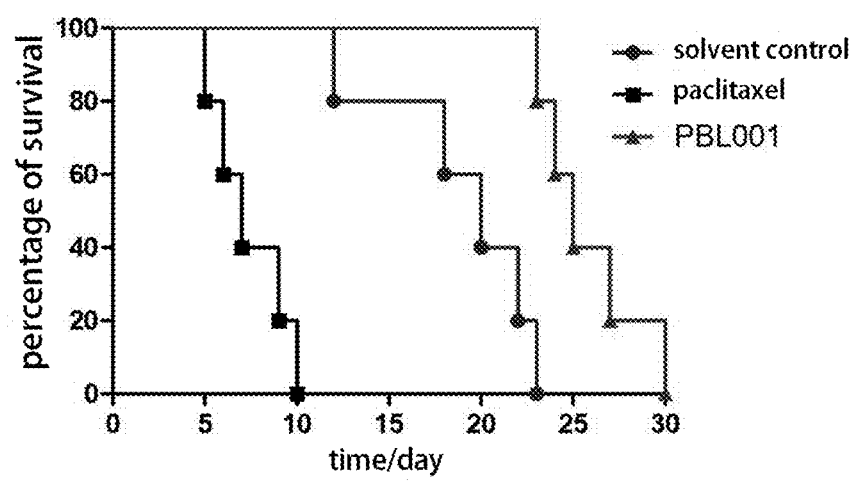
FIG. 13 shows that PBL001 prolongs the survival time of mice in a brain glioma model.

On the first day, $10^6$ U87MG cells were inoculated at the right caudate nucleus of nude mice of 6-8 weeks old. Three days later, a solvent or equal dose of paclitaxel or PBL001 was administered via the tail vein, and the survival time of each group of mice was recorded, as shown in FIG. 13. The results in FIG. 13 showed that as compared with the solvent group or paclitaxel group, PBL001 can significantly prolong the survival time of brain glioma mice in the mouse model, and PBL001 has lower toxic and side effects as compared with paclitaxel.

Described above are only specific embodiments of the present disclosure, but the scope of protection of the present disclosure is not limited to this. Any change or replacement that can be easily conceived by those skilled in the art within the technical scope disclosed in the present disclosure should be covered within the scope of protection of the present disclosure. Therefore, the scope of protection of the present disclosure shall be accorded with the scope of the claims.

The invention claimed is:

1. A brain tumor targeted molecule, comprising a blood-brain barrier crossing region and a tumor target region, wherein the blood-brain barrier crossing region comprises SEQ ID NO: 1.

2. The brain tumor targeted molecule according to claim 1, wherein the tumor target region comprises any combination of CGKRK (SEQ ID NO: 3), ATWLLPPR (SEQ ID NO: 4) and CRGDKGPDC (SEQ ID NO: 7).

3. The brain tumor targeted molecule according to claim 1, wherein the tumor target region comprises an RGD sequence.

4. The brain tumor targeted molecule according to claim 3, wherein the RGD sequence is a linear RGD polypeptide, a cyclic GRD polypeptide or a peptidomimetic compound with an arginine-glycine-aspartic acid tripeptide sequence as an active center.

5. The brain tumor targeted molecule according to claim 4, wherein the amino acid sequence of the tumor target region is CRGDKGPDC (SEQ ID NO:7), and two cysteines form a disulfide bond.

6. The brain tumor targeted molecule according to claim 1, wherein the amino acid sequence of the brain tumor targeted peptide comprises SEQ ID NO: 5, SEQ ID NO: 6 or SEQ ID NO: 8.

7. The brain tumor targeted molecule according to claim 1, wherein the amino acid sequence of the brain tumor targeted peptide comprises SEQ ID NO: 2.

8. A nucleic acid encoding the brain tumor targeted molecule according to claim 1.

9. A nucleic acid construct comprising the nucleic acid according to claim 8, wherein the construct comprises expression cassettes and vectors.

10. A host cell containing the nucleic acid according to claim 8.

11. A host cell containing the nucleic acid construct according to claim 9.

12. A method comprising preparing a brain tumor diagnostic reagent via utilizing the brain tumor targeted molecule according to claim 1.

13. The method according to claim 12, wherein the brain tumor targeted molecule is also connected with an active substance, and the active substance is a diagnostic marker or a tumor therapeutic drug.

14. The method according to claim 13, wherein the active substance connected with the brain tumor targeted molecule comprises fluorescence, isotopes, radioactive substances, or chemotherapeutic drugs.

15. A method comprising preparing a brain tumor therapeutic drug via utilizing the brain tumor targeted molecule according to claim 1.

* * * * *